United States Patent [19]

Hill et al.

[11] 4,054,645

[45] Oct. 18, 1977

[54] RADIODIAGNOSTIC COMPLEXES EMPLOYING FLUORINE-CONTAINING TIN REDUCING AGENTS

[75] Inventors: Brian K. Hill, Cottage Grove, Minn.; Verna M. Kubik, Somerset, Wis.

[73] Assignee: Minnesota Mining and Manufacturing Company, St. Paul, Minn.

[21] Appl. No.: 717,173

[22] Filed: Aug. 24, 1976

[51] Int. Cl.$^2$ .................. A61K 29/00; A61K 43/00
[52] U.S. Cl. ........................ 424/1; 260/429 R; 424/9
[58] Field of Search ................ 424/1, 1.5, 9; 260/429 R

[56] References Cited

U.S. PATENT DOCUMENTS

| 3,466,361 | 12/1969 | Richards et al. | 424/1 |
|---|---|---|---|
| 3,749,556 | 7/1973 | Barak et al. | 424/1 |
| 3,873,680 | 3/1975 | Jackson et al. | 424/1 |
| 3,987,157 | 10/1976 | Molinski et al. | 424/1 |

OTHER PUBLICATIONS

Chervu et al., Radiology, vol. 107, May, 1973, pp. 435–437.
Gil et al., International Journal of Applied Radiation and Isotopes, vol. 27, No. 2, Feb., 1976, pp. 69-72.

*Primary Examiner*—Brooks H. Hunt
*Assistant Examiner*—Christine M. Nucker
*Attorney, Agent, or Firm*—Cruzan Alexander; Donald M. Sell; Warren R. Bovee

[57] ABSTRACT

Radiodiagnostic agents for use in mammalian bodies comprising a radiocomplex which is the reaction product of Tc99m-pertechnetate ion, a diagnostic ligand and a tin (II) reducing agent selected from the group consisting of $SnF_2$, $MSnF_3$, $MSn_2F_5$ and mixtures thereof, wherein M is $NH_4$, Na, K, Li, Rb or Cs. Radiocomplex precursor compositions and methods of making the radiocomplex and radiodiagnostic agents are described.

14 Claims, No Drawings

RADIODIAGNOSTIC COMPLEXES EMPLOYING FLUORINE-CONTAINING TIN REDUCING AGENTS

The present invention relates to diagnostic agents for use in mammalian bodies which are solutions comprising target-specific radiocomplexes containing Tc-99m as the radioactive component. More particularly, the present invention relates to kits for preparing diagnostic radiocomplexes which are more readily prepared in pure form and which have improved storage stability, and to radiocomplexes which have improved reliability, reproducibility and target specificity. The radiocomplexes comprise the reaction product of Tc-99m-pertechnetate ion, a target-specific diagnostic ligand and a fluorine-containing tin (II) salt which is a source of tin (II) ion and which is selected from the group consisting of $SnF_2$, a fluoro-stannate salt such as $MSnF_3$ and $MSn_2F_5$, and mixtures thereof, wherein M is Na, K, $NH_4$, Li, Rb or Cs.

The use of radioactive materials for imaging skeletal bone structure, internal organs and other portions of the mammalian body is known. The use of technetium - 99m (Tc-99m) for radioactively imaging portions of the body and skeleton has proved particularly advantageous due to the low energy gamma radiation and short half life of the radioactive technetium. In use, the Tc-99m is associated with a ligand component to form a radiocomplex. The ligand can be a target-specific ligand, i.e., selected so that when it is injected into the body it will carry the technetium to a specific target in the body or skeleton of a mammal. When the radiocomplex is injected or otherwise introduced into the body and has become localized in the target, scanning the body for radioactivity can reveal information regarding the structure or function of the target organ, identify areas of increased skeletal uptake, or otherwise provide diagnostic information. These techniques and materials have become widely known in the art as evidenced by U.S. Pat. No. 3,852,414 issued Dec. 3, 1974, and the reference cited at Column 1 therein.

For clinical use it is common practice to provide the reducing agent and the diagnostic ligand together as a "kit" which comprises a container, usually a glass vial, having therein a reducing agent such as a source of tin (II) ion, for example a solution of stannous chloride ($SnCl_2$), and a ligand component which is a target-specific ligand which can complex with technetium. Just prior to use, the ligand is radioactively labeled by aseptically introducing a solution containing Tc-99m-pertechnetate ion such as can be obtained from a Tc-99m generator in the conventional manner. The tin (II) ion reduces the pertechnetate ion and permits the technetium to associate or complex with the ligand component to radioactively "label" the ligand material.

The radiodiagnostic solution thus prepared can then be injected into the mammalian organism whereupon the radiocomplex migrates to, and localizes in, a selected target portion of the body and can provide an image or other information about the body when the body is scanned for radioactivity with appropriate apparatus such as a rectilinear scanner or gamma camera.

While the use of these radiocomplexes has proven to be a useful diagnostic technique, their use is attended by a variety of difficulties. The use of $SnCl_2$ as the source of tin (II) ions for reduction of pertechnetate poses several problems. The $SnCl_2$ is difficult to obtain and maintain pure in kit form since it readily oxidizes or hydrolyzes. This degradation can cause the production of undesirable alternate species or by-products in the kits. This in turn can provide undesirable body background and unclear organ outline due to excessive uptake of the resulting radiocomplexes in non-target areas of the body.

The present invention overcomes the disadvantages associated with the formation of Tc-99m-containing diagnostic radiocomplexes using stannous chloride reducing agents. More paritcularly the present invention relates to Tc-99m-containing diagnostic radiocomplexes and the method of preparing these radiocomplexes using a unique class of fluorine-containing tin (II) salts. Surprisingly, the fluorine-containing tin (II) salts employed in this invention exhibit improved resistance to hydrolysis and oxidation compared with the previously used stannous chloride reducing agents yet are capable of readily reducing pertechnetate to allow formation of useful diagnostic radiocomplexes. These seemingly contradictory properties provide radiodiagnostic solutions having superior target specificity, i.e. lower uptake in non-target areas of the body. Further, the precursor components or "kits" used to prepare the radiodiagnostic solutions can be formulated and stored at room temperatures for prolonged periods of time without significant degradation. In contrast, prior art kits employing $SnCl_2$ reducing agents are subject to significant degradation during handling and storage and therefore are formulated using greater initial amounts of reducing agent containing potentially toxic tin. Moreover, these kits have to be maintained under refrigerated conditions to minimize degradation.

The radiodiagnostic solutions of the present invention are solutions containing radiocomplexes which are the reaction product of (a) radioactive pertechnetate ion with (b) a target-specific diagnostic ligand, and (c) a reducing agent which is a fluorine-containing tin (II) salt which is a source of tin (II) ion and which is selected from the group consisting of stannous fluoride ($SnF_2$) and a fluorostannate salt such as $MSnF_3$ or $MSn_2F_5$, and mixtures thereof, wherein M is Na, K, $NH_4$, Li, Rb or Cs. The radiodiagnostic solutions are preferably sterile, aqueous isotonic solutions such as an isotonic saline solution or the like.

When the radioactive Tc-99m-pertechnetate ion ($99mTcO_4^-$) is admixed in aqueous solution with the target-specific diagnostic ligand and a source of tin (II) ion, the tin (II) ion is believed to act as a reducing agent to lower the oxidation state of the pertechnetate so that the resulting technetium (Tc-99m) will form a complex with the diagnostic ligand. The radioactive pertechnetate ion is reduced by the tin (II) ion to a technetium species having an oxidation state greater than 0 and less than +7. This reduction is followed by the formation of a chemical complex of the technetium with the target-specific ligand. The reduction and complexing reactions are conveniently carried out in aqueous solution at room temperature.

The radioactive pertechnetate ion ($99m\ TcO_4^-$) is well known to the radiodiagnostic art. A solution of the pertechnetate ion useful in the present invention can be obtained from a technetium generator in the conventional manner. Eluting or "milking" the generator with an aqueous medium will provide a sterile, non-pyrogenic solution containing pertechnetate in the form of $M^x(99m\text{-}TcO_4^-)_x$, wherein $M^x$ is a pharmaceutically acceptable cation such as a proton, an alkali metal ion, an ammonium ion or the like and most preferably sodium or ammonium, and wherein x is a positive integer less than four. Typically, the aqueous elution medium is a saline solution which provides sodium 99m pertechnetate (Na 99mTcO$_4$).

The target-specific diagnostic ligands which are useful in the present invention are, per se, well known in the art. The literature is replete with reference to various compounds which can complex with technetium in the presence of tin (II) and thereafter be injected into the body and localize in a desired area thereof. A partial list of such compounds would include those listed in U.S. Pat. No. 3,852,414 issued Dec. 3, 1974: sodium pyrophosphate, long chain polyphosphates, tripolyphosphate, cyclic or ring metaphosphates of the formula P$_n$O$_{3n}$$^{-n}$, chelating agents, red blood cells, and proteins including albumins; sulfur-containing compounds described in U.S. Pat. No. 3,873,680 issued Mar. 25, 1975, including N-acetyl-penicillamine, 2-mercaptoethanol, 3-mercaptopropanol, 4-mercaptobutanol, 4-mercapto-2-methyl-2-butanol, 2-mercaptoethylamine, 6,8-dihydrothioctic acid, alpha-thio-2-furan pyruvic acid, p-mercaptobenzoic acid; 2,3-dimercaptosuccinic acid. Other useful known diagnostic ligands would include diethylenetriamine pentaacetate salts such as the pentasodium and calcium trisodium salts, imidodiphosphate, ethyl-1 hydroxy-1,1-diphosphonate (EHDP), methylene diphosphonate (MDP), diethylenetriamine penta(methylene phosphonic acid) (DTPMP), penicillamine, cysteine, phytic acid, mercaptoisobutyric acid, monomercaptosuccinic acid, diethylene triamine pentaacetic acid (DTPA), N-(2,6 dimethyl phenyl carbamoylmethyl) iminodiacetic acid (HIDA).

As can be appreciated, the useful diagnostic ligand components are quite numerous. Compounds in addition to those listed above can be used if they can form stable complexes with technetium and exhibit target specificity in the body. Compounds having the requisite target specificity can be selected by known techniques such as by the determination of partition coefficients and the like.

Exemplary materials which form stable complexes with technetium and posses the required target specificity are sodium pyrophosphate (Na$_4$P$_2$O$_7$.10H$_2$O), 2,3-dimercaptosuccinic acid (DMSA), and 6,8-dihydrothioctic acid (DHTA) which provide target specificity for bone, kidney and liver-gall bladder respectively. As noted previously these materials are readily available and are per se well known in the radiodiagnostic art. For example, the use of Tc-99m labeled pyrophosphate as a bone-scanning radiodiagnostic agent is described in Krishnamurthy et al., "Kinetics of 99m Tc - Labeled Pyrophosphate and Polyphosphate in Man," *Journal of Nuclear Medicine*, Vol. 16, Number 2, pp. 109–115 (1975), and other references cited therein. U.S. Pat. No. 3,873,680 issued Mar. 25, 1975, discloses the use of technetium - 6,8-dihydrothioctic acid complexes as liver and gall bladder specific radiodiagnostic agents. The use of 2,3- dimercaptosuccinic acid is described in an article by Handmaker et al., "Clinical Experience with 99m-Tc DMSA (Dimercaptosuccinic Acid), A New Renal Imaging Agent," *Journal of Nuclear Medicine*, Vol. 16, No. 1, pp. 28–32 (1975).

Because the pertechnetate ion does not itself directly form stable complexes with the target-specific diagnostic ligand, the pertechnetate ion must be reduced to a lower valence state by an in situ reducing agent such as a tin (II) ion. The reducing agents described in this invention provide a stable source of tin (II) ion in a readily prepared and purified form. The salts which act as a source of tin (II) ion, and hence a reducing agent, in the present invention are the fluorine containing tin (II) salts selected from the group consisting of stannous fluoride (SnF$_2$), M trifluorostannate (MSnF$_3$), and M pentafluoro distannate (MSn$_2$F$_5$), and mixtures thereof, wherein M is ammonium (NH$_4$) or an alkali metal, such as sodium (Na), potassium (K), lithium (Li), rubidium (Rb) or cesium (Cs).

Stannous fluoride is readily available. The other stannate salts, MSnF$_3$ and MSn$_2$F$_5$, can be readily prepared by the addition of alkali metal fluoride or ammonium fluoride to a solution of tin (II) fluoride. The MSn$_2$F$_5$ compounds can be prepared by the addition of the M fluoride to a solution of tin (II) fluoride unitl the SnF$_2$:MF ratio is about 2:1. The precipitate which forms can be filtered, washed and dried.

The MSnF$_3$ compounds are prepared by admixing solutions of tin (II) fluoride and a slight excess of M fluoride (slightly in excess of a 1:1 ratio). Crystallization provides the MSnF$_3$ compound. A detailed discussion of the preparation and analysis of these compounds can be found in Donaldson, J. D. and O'Donoghue, J. D., "Complex Tin (II) Fluorides," *Journal of the Chemical Society*, pp. 271–275 (1964). Stannate salts where M is sodium or potassium are preferred because of superior solubility properties and compatibility with mammalian bodies.

The diagnostic radiocomplex agents of this invention can be prepared by reacting the pertechnetate, the tin (II) reducing agent and the diagnostic ligand together in aqueous solution. The reduction of the pertechnetate by the tin (II) and the complexing of the components takes place at room temperature, usually within about 5 to 15 minutes.

Because of the short half-life of technetium 99m and the desire to minimize operator exposure to radioactive materials, it is preferred to generate and admix the radioactive pertechnetate ion with the diagnostic ligand and the tin (II) source within about eight hours prior to use. Accordingly, precursor compositions or "kits" comprising the tin (II) source and the diagnostic ligand in solution or dried form are generally prepared for clinical use. These kits comprise an ampule or a glass vial typically having a volume of about 1 to 25 cc and sealed by a septum and having aseptically distributed therein a solution, or preferably a freeze dried mixture, of appropriate amounts of the tin (II) reducing agent and the diagnostic ligand to prepare a radiodiagnostic solution. The technetium in the form of a solution containing Tc-99m-pertechnetate ion is obtained by the elution of a technetium generator with saline solution. These generators and elution techniques are well known in the art. See, for example, U.S. Pat. No. 3,873,680, issued Mar. 25, 1975, for a description of these materials and techniques.

The pertechnetate containing solution is then charged to the kit, such as by injection with a syringe through the septum. The reduction of the pertechnetate and the radioactive labeling of the diagnostic ligand occurs to form a target-specific radiocomplex. The resulting radiodiagnostic solution can then be withdrawn from the kit with a syringe and injected into the body for scanning and diagnosis.

Alternatively, the components may be furnished as a multi-part kit where appropriate amounts of each of the components is separately packaged in sterile vials or ampules and admixed just prior to use, for example, where undesirable precipitates may be formed by admixture of the ligand and reducing agent components prior to labeling.

The amount of each of the components used in preparing the radiodiagnostic solutions can vary. It is desirable to have sufficient quantities of reducing agent and diagnostic ligand present to reduce all of the pertechnetate ion contained in the eluate from the technetium generator and to complex the reduced technetium. Thus, the reactants, or the prepared kits, are typically formulated to contain a large molar excess of the reducing agent over the pertechnetate ion, e.g. up to $10^6$ and preferably $10^5$ to $10^6$ moles reducing agent per mole of pertechnetate ion. An excess of reducing agent is desirable to ensure that the pertechnetate is maintained at a reduced oxidation state. Due to equilibrium considerations the percent of diagnostic ligand which is labeled by a given amount of the technetium is increased when a large excess of tin (II) reducing agent is employed.

The mole ratio of diagnostic ligand to tin (II) reducing agent is preferably about 1:1 or greater and most preferably is in the range of about 1:1 to about 5:1 moles of diagnostic ligand per mole of reducing agent. Thus, a typical kit may contain the diagnostic ligand and reducing agent in these ratios.

The actual amount of Tc-99m pertechnetate ion which must be added to the components in the kit to provide a useful radiodiagnostic solution can vary greatly and is not critical. Sufficient technetium should be present in the final solution to provide adequate imaging. The required amount can vary depending on several factors, e.g., (1) the mammal species to be studied; (2) the resolution power of the imaging device used; and (3) the needs of the individual researcher or clinician. The amount of radioactive 99m-pertechnetate ion per milliliter of solution eluted from a Tc-99m generator decreases with the age of the generator and, accordingly, it becomes necessary to elute larger volumes in order to obtain the same amount of radioactivity. The radioactivity of the elution can be easily assayed with a conventional gamma detector.

Because the specific activity of the eluate can vary with time, and because the needs of each user will vary, it is difficult to set exact limits on the amount of Tc-99m eluate which must be added to each unit of the other components or to each prepared kit. It is generally desired to provide sufficient radioactive technetium so that the researcher can obtain about 500,000 counts in a 1 to 5 minute diagnosis. Typical diagnostic solutions may contain from about 100 microcuries to 50 millicuries per milliliter of radiodiagnostic solution, preferably from about 1 to 5 millicuries per milliliter. A total amount of 2 millicuries of radioactive material typically suffices for test purposes in the average (e.g. 70 kg) human. Only about $0.02 \times 10^{-10}$ gram of 99m-pertechnetate dissolved in a milliliter of aqueous medium (e.g. isotonic saline) is needed to provide 0.1 MCi/ml, and less than $100 \times 10^{-10}$ gram ($10^{-10}$ gram-atoms) of 99m-pertechnetate per milliliter of solution provides enough radioactivity for most uses. Generally amounts of generator eluate ranging from about 1 to about 10 ml are added to the freeze-dried contents of a kit as this provides sufficient radiodiagnostic solution for most purposes.

In order to minimize any precipitation of the compounds prior to formation of the radiodiagnostic complex, it may be beneficial to maintain the pH of the other admixed components, e.g. a kit, in the acid range, e.g. pH 2 to 7 and preferably pH 3 to 5. Following formation of the radiocomplex, the pH need not be maintained in the acid range. It is preferred to maintain the pH of the radiodiagnostic solutions as nearly neutral as possible to minimize adverse reaction when the solution is injected into the body. However, due to the relatively small amounts employed, solutions having a pH within the ranges noted above do not cause excessive irritation when injected into the body. The adjustment of the pH can be readily accomplished with any acid or base which will form water-soluble salts. Preferably hydrochloric acid or sodium hydroxide is used. The pH of the solutions used to prepare the kits described herein is generally adjusted prior to lyophilization and no further pH adjustment is necessary when the radiodiagnostic solutions are subsequently prepared.

After injection into the body, the diagnostic radiocomplex solution is carried through the bloodstream and, depending on the nature of the diagnostic ligand, will localize in the bones, kidneys, liver, gall bladder, or other portion of the body. The time required to localize in the body so that meaningful imaging and diagnosis can occur will vary depending on the target area of the body. Typically, diagnostic scanning can be undertaken within about 30 minutes to 4 hours after injection.

As noted previously, the fluorine-containing tin (II) salts provide a more stable source of stannous ion and therefore a more stable kit than those prepared using reducing agents such as stannous chloride. The stability of the kit components is of great importance in the preparation of a radiodiagnostic agent. As noted previously herein, the degradation of other commonly used reducing agents, such as stannous chloride, results in the formation of undesirable radiocomplex species or by-products which do not have the desired target specificity when injected into the body. The presence of these by-products is associated with the appearance of background images when the body is scanned, resulting in lack of clear definition of the intended target.

On manifestation of the stability of kits prepared according to the present invention is the percent of tin remaining as tin (II) after prolonged storage at room temperature. Typically, a kit will retain about 80-85 percent of the initial tin (II) after mixture and lyophilization. After prolonged storage, e.g. 9 months or more, the kits of the present invention retain about 90% of the tin (II) present after lyophilization, i.e. about 75% of the original tin (II) present prior to lyophilization. In contrast, a commercially available bone kit retains only about 50 percent of the initial amount of stannous chloride reducing agent after lyophilization and 8 months of refrigerated storage.

The present invention will be further described by reference to the following illustrative examples. In these examples the total injected dose was determined by counting the radioactive emissions over a given time period for each of the portions of the sacrificed animal, including the urine and feces, and summing these counts. The percent injected dose present in a particular portion is then determined by dividing the counts from that portion by the total counts for the animal.

Bone:tissue ratios are determined on the hind leg of the animal. These are calculated as counts per gram of tibia and fibula divided by the counts per gram of surrounding tissue.

EXAMPLE 1

Kits useful for preparing radiodiagnostic solutions for imaging the skeletal portions of a mammal body were prepared. Radiodiagnostic solutions prepared according to the present invention which comprise a radiocomplex containing a pyrophosphate diagnostic ligand were compared with solutions containing a radiocomplex which did not contain the pyrophosphate ligand.

Solutions were prepared as follows:

Solution 1 — 500 mg $Na_4P_2O.10H_2O$ were dissolved in 50 ml of sterile water for injection. One ml of this solution contained 10 mg $Na_4P_2O_7.10$ $H_2O$, the amount needed for one kit.

Solution 2 — 17.3 mg $SnF_2$ was dissolved in 50 ml of sterile water for injection. One ml of this solution contained $2.2 \times 10^{-3}$ m. moles $Sn^{+2}$, the amount needed for one kit.

Solution 3 — 9.2 mg of NaF were dissolved in 100 ml of sterile water for injection. One ml of this solution contained $2.2 \times 10^{-3}$ m. moles of NaF.

Kits containing radiocomplex precursor materials were prepared from the above solutions.

Kit A: To 1.0 ml of Solution 2 was added 1.0 ml of Solution 3 followed by 1.0 ml of Solution 1. The contents were mixed by shaking.

Kit B: To 1.0 ml of Solution 1 was added 1.0 ml of Solution 2 with shaking.

Kit C: To 1.0 ml of Solution 2 was added 1.0 ml of Solution 3 and the mixture shaken.

Radiodiagnostic solutions for injection were prepared by adding to each kit 1.25 ml of saline eluate, from a Tc-99m generator, which contained 100μ curies/ml of Tc 99m-pertechnetate ion. The solution in each kit was then made up to 5 ml total volume by the addition of sterile water. Mice were injected with each kit solution and metabolic distribution of radioactivity was determined after one hour. The results reported as percent injected dose of radioactive component are summarized as follows:

|       | Liver | Bone | Tissue | Bone:Tissue |
|-------|-------|------|--------|-------------|
| Kit A | 2.3%  | 0.9% | 0.1%   | 61:1        |
| Kit B | 1.7   | 0.5  | 0.1    | 49:1        |
| Kit C | 58.1  | 0.2  | 0.04   | 18:1        |

Kits A and B prepared according to the present invention provided good bone to tissue ratios with relatively low liver uptake. Kit C which did not contain the bone specific pyrophosphate ligand provided overall lower bone uptake and lower bone-to-tissue ratios. The use of Kit C also provided extremely high liver uptake. Thus, while all three kits were able to reduce technetium and provide a bone-seeking complex, the compositions of the present invention, which included a bone-specific ligand, gave superior results as evidenced by lower liver uptake and higher bone to tissue ratios.

EXAMPLE 2

A comparison of the heat aging characteristics of the kits of the present invention with prior art kits was performed as follows. Bone kits were prepared using $NaSnF_3$ and $NaSnCl_3$ as the reducing agent. Solutions were prepared in a dry box as follows:

Solution 1 — 500 cc $Na_4P_2O_7$ solution was prepared by dissolving 10.00 gr. $Na_4P_2O_7$ in about 450 cc sterile water, adjusting pH to 5.0 with 6N HCl. The solution was diluted with water to 500 ml.

Solution 2 — 0.100 gm $SnCl_2$ 19 $2H_2O$ and 0.26 gm NaCl were dissolved in 100 ml sterile water and diluted with sterile water for injection to 100 cc volumetric flask.

Solution 3 — 0.093 gm $NaSnF_3$ solution was dissolved in 100 ml of sterile water.

Kits containing radiocomplex precursor materials were prepared from the above solutions.

Kit A: 250 cc of solution 1 and 100 cc of Solution 3 were combined. The pH was 4.74. The solution was dispensed in 1 ml quantities in a group of 64 vials.

Kit B: 250 cc of solution 1 and 100 cc of solution 2 were mixed and the procedure of Kit A was repeated.

Each of the vials was capped with a lyophilization stopper as filled, sealed with an aluminum overseal and frozen.

Twenty vials from each group were randomly selected and steam sterilized in an autoclave for 15 minutes at 121° C after which the vials were again frozen. The vials were then opened with minimum exposure to oxidation, allowed to thaw and placed in the lyophilizer. After lyophilization, the vials were sealed under nitrogen and placed in refrigerated storage.

Solutions were prepared from the kits by injecting saline solution containing Tc-99m-pertechnetate into the kits. Mice were injected with these kits. Metabolic distribution of radioactivity was determined after 2 hours and summarized as follows:

|       |                    | Reducing Agent | Liver | Stomach | Bone:Tissue |
|-------|--------------------|----------------|-------|---------|-------------|
| Kit A |                    | $NaSnF_3$      | 1.8%  | 2.7%    | 72:1        |
| Kit B |                    | $NaSnCl_3$     | 12.1  | 5.6     | 80:1        |
| Kit A | Steam Sterilized   | $NaSnF_3$      | 1.2   | 5.8     | 42:1        |
| Kit B | Steam Sterilized   | $NaSnCl_3$     | 19.4  | 37.9    | 2:1         |

These experiments demonstrate the stability of kits prepared according to the present invention when exposed to accelerated heat aging (steam sterilization). While the properties of kits using $NaSnF_3$ and $NaSnCl_3$ as reducing agents were initially comparable, the accelerated aging data indicated that the kits using the stannous chloride reducing agent were degraded. This was evidenced by relatively high concentration of radioactive component in the stomach, indicating the presence of free (unreduced) technetium in the injected solution, and by greatly reduced bone-to-tissue ratios. The kits of the present invention underwent the severe aging conditions with relatively little degradation.

EXAMPLE 3

A kit for providing a radiodiagnostic solution suitable for imaging kidneys was prepared as follows:

Ninety milligrams of dimercaptosuccinic acid and 20 mg $NaSnF_3$ were weighed and transferred to a 100 ml volumetric flask. The flask was flushed with nitrogen and transferred to a drybox under a nitrogen atmosphere. The flask was filled to the mark with sterile $H_2O$ for injection and shaken and warmed slightly until all the solid had dissolved. The resulting solution was 5 mmolar in DMSA and 1 mmolar in $Sn^{+2}$. Kits were prepared by dispensing 2 cc of the solution into 10 cc vials. The vials were stoppered, transferred from the drybox and frozen. The contents of each kit was then lyophilized.

The contents of each of the kits was diluted to a total volume of 5.0 cc with normal saline and a volume of Tc 99m-pertechnetate in saline sufficient to provide 25 to 50 $\mu$Ci/ml. One-tenth of a cc of the solution was injected per mouse and metabolic distribution of radioactivity after 2 hours was determined. The results are summarized as follows:

|  | % injected dose |
|---|---|
| Lungs | 0.6 |
| Liver | 7.1 |
| Spleen and pancreas | 0.3 |
| Kidneys | 26.6 |
| Stomach and gut | 4.4 |
| Heart | 0.3 |
| 0.3 cc blood | 1.8 |
| Carcass | 18.5 |
| Urine and feces | 40.1 |

These results indicated an acceptable kidney imaging agent.

EXAMPLE 4

Radiodiagnostic solutions for imaging bones using $SnF_2$ and $NaSnF_3$ as the reducing agents were prepared as follows:

Solution A ($NaSnF_3$ reducing agent)

0.1g $Na_4P_2O_7 \cdot 10H_2O$, 0.035 g $SnF_2$, and 0.009 g NaF were dissolved in 400 ml saline for injection. The initial pH of the mixture was 5.2 and was adjusted to 7.0 with .01N NaOH before diluting to 500 ml with normal saline. 5.0 ml of this solution was placed in each of 4–20 cc vials. One of the vials was labelled with Tc 99m-pertechnetate and used immediately. The other three were placed in a freezer. The remainder of the stock solution was placed in polyethylene bottles and stored overnight at room temperature.

Solution B ($SnF_2$ reducing agent)

0.1 g $Na_4P_2O_7 \cdot 10H_2O$ and 0.035 g $SnF_2$ were placed in another 500 ml flask and treated identically to the solutions described above.

Mice were injected with each of the two radiodiagnostic solutions prepared above and metabolic distribution of radioactivity was determined. The distribution indicated these solutions were satisfactory as bone imaging agents.

Two kits of each of the frozen solutions of A and B were prepared by lyophilization as described hereinbefore. Radiodiagnostic solutions were prepared from the kits by addition of saline solution containing Tc 99m-pertechnetate to the vial. Mice were injected with the radiodiagnostic solution and the metabolic distribution determined after two hours. Kit A showed 4.9% and 6.1% in the liver with bone:tissue ratios of 36:1 and 40:1, while B showed 1.3% and 1.2% in the liver with bone:-tissues of 86:1 and 53:1.

EXAMPLE 5

A radiodiagnostic solution for imaging the liver and gall bladder was prepared using 6,8-dihydrothioctic acid as the diagnostic ligand and sodium trifluorostannate as the reducing agent.

To vials containing 2.3 mg of 6,8-dihydrothioctic acid was added 1 ml of an aqueous solution containing 4.91 mg sodium bicarbonate, 1 ml ethanol and 1 ml of an aqueous solution containing 0.44 mg sodium trifluorostannate. A quantity of saline solution containing Tc 99m-pertechnetate ion was added to each vial in sufficient quantity to provide 250 $\mu$Ci per vial.

After 20 minutes the solutions were injected into mice and metabolic distribution determined at 5 minutes, 1 hour and 2 hours. The results showed sufficient localization in the liver and gall bladder to provide useful diagnostic images.

EXAMPLE 6

A radiodiagnostic solution for skeletal imaging was prepared using sodium pentafluorodistannate as the reducing agent. A first solution was prepared under nitrogen by dissolving 10 grams of sodium pyrophosphate decahydrate, $Na_4P_2O_7 \cdot 10H_2O$, in 450 ml deaerated sterile water for injection. The pH was adjusted to 5.1 with 6N hydrochloric acid. The volume was adjusted to 500 ml with sterile water.

A second solution was prepared by dissolving 0.44 grams of sodium pentafluorodistannate in 500 ml of sterile water.

Kits were prepared by mixing the two solutions, filtering the resulting solution through a 0.2$\mu$m filter, and dispensing 1 cc of the solution into 10 cc pharmaceutical vials. The filled vials of the bone agent were lyophilized and sealed under nitrogen for storage.

The contents of a kit was radioactively labeled by adding to each kit a saline solution containing sufficient Tc 99m-pertechnetate ion to count skeletal portions of mice. The efficacy of the labeled kit was tested by injecting the prepared solution into a Swiss Webster mouse. After two hours the mouse was sacrificed and the biological distribution was determined. The percent injected dose in the liver was found to be 1.5 percent. The bone:tissue ratio was 58:1. These results indicate the kit provided a satisfactory bone-imaging radiodiagnostic solution.

EXAMPLE 7

A radiodiagnostic solution for kidney imaging was prepared using sodium pentafluorodistannate as the reducing agent and 2,3-dimercaptosuccinic acid (DMSA) as the diagnostic ligand. A first solution was prepared in a nitrogen atmosphere by dissolving 1.2 g of 2,3-dimercaptosuccinic acid in 400 ml of absolute ethanol and diluting to 1500 ml with sterile water for injection.

A second solution was prepared by dissolving 0.264 g of sodium pentafluorodistannate in 500 ml of sterile water for injection.

Kits were prepared by mixing the two solutions, filtering through a 0.2$\mu$m filter and dispensing 3 cc of the solution into 10 cc pharmaceutical vials. The filled vials of the kidney agent were lyophilized and sealed under nitrogen for storage.

The contents of the kits were radioactively labeled by adding to each kit a saline solution containing sufficient Tc 99m-pertechnetate ion to count the kidneys of rats. The efficacy of the labeled kits was tested by injecting the prepared solutions into twelve rats 15–30 minutes after labeling. Biological distribution was determined in six of the rats after two hours by sacrificing the rats and counting the radioactivity in the various portions of the rats. Similar distribution data was obtained on the remaining six rats sacrificed after four hours. The results are shown below wherein the values are given as percent injected dose. The kidney:liver ratios are based on counts per gram of tissue in the kidneys divided by the counts per gram of tissue in the liver.

| Organ | 2 hours after injection | 4 hours after injection |
|---|---|---|
| Liver | 4.3 | 6.5 |
| Kidneys | 52 | 38.7 |
| Carcass | 21.6 | 25.8 |
| Urine & Feces | 15.3 | 21 |
| Blood | 6.8 | 7 |
| Kidney:Liver Ratio | 53:1 | 23:1 |

These data show that the kits provided a satisfactory kidney-imaging radiodiagnostic solution.

EXAMPLE 8

A pharmaceutical kit for imaging skeletal structure in mammals was prepared by dissolving 1.86 g of $Na_4P_2O_7 \cdot 10H_2O$ in 750 ml of sterile water. To this solution was added 0.351 g of stannous fluoride and 250 ml of sterile water. After the solution was thoroughly mixed and became clear it was filtered through a 0.2 micrometer filter.

10 ml of the solution was introduced into each of seven, 20 ml glass vials. The vial contents were frozen in a dry-ice and acetone mixture and lyophilized.

The contents of the vials were radioactively labeled by adding a saline solution containing sufficient Tc 99m-pertechnetate to count the skeleton of mice. The efficacy of the solution was tested by injecting the solutions into mice and determining biological distribution after two hours. The solutions were found to provide satisfactory bone:tissue ratios.

What is claimed is:

1. An intravenously injectable diagnostic solution for use in mammalian bodies which is an aqueous solution comprising a target-specific radiocomplex, said radiocomplex comprising the reaction product of an aqueous mixture of (a) Tc99m-pertechnetate ion, (b) a target-specific diagnostic ligand, and (c) a tin (II) reducing agent for said pertechnetate ion selected from the group consisting of $SnF_2$, $MSnF_3$ and $MSn_2F_5$, and mixtures thereof, wherein M is $NH_4$, Na, K, Li, Rb or Cs.

2. A diagnostic solution according to claim 1 wherein said aqueous solution comprises sterile, aqueous, isotonic saline solution.

3. A radiodiagnostic solution according to claim 1 having a pH in the range of 2 to 7.

4. A diagnostic solution according to claim 1 wherein said radiocomplex comprises the reaction product of a diagnostically sufficient amount of Tc99m-pertechnetate ion and a molar excess of reducing agent, and wherein the ratio of moles of diagnostic ligand to moles of reducing agent is greater than about 1:1.

5. A diagnostic solution according to claim 1 wherein said diagnostic ligand is selected from the group consisting of sodium pyrophosphate, 2,3-dimercaptosuccinic acid and 6,8-dihydrothioctic acid.

6. An aseptic, stable pharmaceutical composition for the preparation of an intravenously injectable radiodiagnostic solution containing a target-specific radiocomplex for mammalian bodies, said composition being a radiocomplex precursor composition comprising a mixture of a target-specific diagnostic ligand and a fluorine-containing tin (II) compound selected from the group consisting of $SnF_2$, $MSnF_3$, $MSn_2F_5$, and mixtures thereof wherein M is $NH_4$, Na, K, Li, Rb or Cs.

7. A composition according to claim 6 wherein said radiocomplex precursor is a freeze-dried solid.

8. A composition according to claim 6 wherein said radiocomplex precursor is contained in a sterile, aqueous isotonic saline solution.

9. A composition according to claim 6 wherein the ratio of moles of diagnostic ligand to moles of fluorine-containing tin (II) compound is greater than about 1:1.

10. A composition according to claim 9 wherein said fluorine-containing tin (II) compound is present in an amount in excess of the theoretical amount required to reduce a diagnostically sufficient amount of Tc-99m-pertechnetate ion.

11. A composition according to claim 6 wherein said target-specific diagnostic ligand is selected from the group consisting of sodium pyrophosphate and 2,3-dimercaptosuccinic acid.

12. A process for the preparation of a target-specific radiocomplex for use in mammalian body diagnosis comprising
 a. reducing, in aqueous solution, Tc-99m-pertechnetate ion to a 99m-technetium species having an oxidation state greater than zero but less than +7 with a reducing agent comprising a fluorine-containing tin (II) compound selected from the group consisting of $SnF_2$, $MSnF_3$, $MSn_2F_5$, and mixtures thereof, wherein M is $NH_4$, Na, K, Li, Rb or Cs,
 b. complexing said reduced 99m-technetium species with a target specific radiodiagnostic ligand.

13. A process according to claim 12 wherein said tin (II) compound and said diagnostic ligand are prepared in kit form as a freeze-dried mixture in an aseptically sealed vial and wherein an aqueous solution containing said Tc-99m-pertechnetate ion is injected into said vial.

14. A process according to claim 12 wherein said target-specific diagnostic ligand is selected from the group consisting of sodium pyrophosphate, 6,8-dihydrothioctic acid and 2,3-dimercaptosuccinic acid.

* * * * *